United States Patent
Pott et al.

(10) Patent No.: US 6,581,906 B2
(45) Date of Patent: Jun. 24, 2003

(54) CONNECTOR HAVING AN INNER DISPLACEMENT MEMBER

(75) Inventors: Harald Pott, Wipperfuerth (DE); Helmut Schmidt, Oberthal (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/803,018

(22) Filed: Mar. 12, 2001

(65) Prior Publication Data

US 2001/0020787 A1 Sep. 13, 2001

(30) Foreign Application Priority Data

Mar. 10, 2000 (DE) .......................................... 100 11 724

(51) Int. Cl.⁷ ................................................ F16K 51/00
(52) U.S. Cl. ...................... 251/149.1; 604/256; 604/905
(58) Field of Search ........................... 251/149.1, 149.6; 604/905, 256, 523, 93.01

(56) References Cited

U.S. PATENT DOCUMENTS

| | | | | |
|---|---|---|---|---|
| 1,700,632 A | * | 1/1929 | Gay ........................ | 251/149.1 |
| 1,810,735 A | * | 6/1931 | Smith ...................... | 251/149.1 |
| 3,806,086 A | * | 4/1974 | Cloyd ...................... | 251/149.7 |
| 4,745,950 A | * | 5/1988 | Mathieu ..................... | 604/905 |
| 4,903,942 A | * | 2/1990 | Licciardello et al. ..... | 251/149.1 |
| 5,320,326 A | * | 6/1994 | Ju et al. ................... | 251/149.1 |
| 5,535,985 A | * | 7/1996 | Larbuisson ............... | 251/149.1 |
| 5,738,144 A | * | 4/1998 | Rogers ..................... | 251/149.1 |
| 5,749,861 A | * | 5/1998 | Guala et al. ................ | 604/256 |
| 5,806,832 A | * | 9/1998 | Larbuisson ............... | 251/149.6 |
| 5,848,994 A | | 12/1998 | Richmond .................. | 604/248 |
| 6,039,302 A | * | 3/2000 | Cote, Sr. et al. ......... | 251/149.1 |

FOREIGN PATENT DOCUMENTS

| | | |
|---|---|---|
| EP | 0 383 355 | 8/1990 |
| EP | 0 569 030 | 11/1993 |
| EP | 0 798 013 | 10/1997 |
| WO | 97/05921 | 2/1997 |

* cited by examiner

*Primary Examiner*—Ehud Gartenberg
*Assistant Examiner*—John Bastianelli
(74) *Attorney, Agent, or Firm*—Jacobson Holdman PLLC

(57) ABSTRACT

The invention relates to a connector which has an inner displacement member. The flow is stopped by the connector, i.e. the connector is impervious, in a first position. In a second position of the displacement member, with a stop defining the position, flow apertures are released which release the flow into the flow carrying line.

8 Claims, 2 Drawing Sheets

CONNECTOR HAVING AN INNER DISPLACEMENT MEMBER

BACKGROUND OF THE INVENTION

1. Field of the Invention

The invention relates to a connector having an inner displacement member which prevents the flow of a liquid from a pouch into a hose system in a first state and which only allows the flow after displacement.

2. Description of the Related Art

It is known in the prior art to allow the flow from systems in sterile packaging through a hose only on application. In EP 0 038 355 A1, a break-off pin is located at the inside of the hose which is broken off to release the flow and should then wedge transversely in the hose. The disadvantage of this design is the possibility that minute breakage particles can enter the solution and thus the place of application, which causes unpleasant side effects for the patients, particularly with intra-peritoneal solutions or infusion solutions. Puncture membranes are also known which have the same disadvantages.

Inner displacement members in adapters are also known from EP 0 798 013 A1 where the displacement member is reversibly supported in the adapter. The displacement member is pushed back into the starting position over and over again without any external influence due to the resilient force of an inner spring. The design of such a displacement member is very complex and expensive to manufacture and therefore can not be used in disposable systems.

SUMMARY OF THE INVENTION

It is the object of the present invention to provide a disposable connector, preferably for connection to medical apparatuses, which is simple to manufacture at a low price and which prevents the flow in a first state and allows the flow after the irreversible switch into a second state. The object is solved by a connector having hose connections at the proximal end and the distal end, and having an inner displacement member which is movable in the axial direction of the connector. An inner lumen allows flow therethrough with at least one outlet aperture and at least one flow aperture which is impervious to flow in a first position. The inner displacement member has a stop in order to define a second fixed position at which at least one flow aperture is opened for flow.

Solutions, for example disinfecting solutions, infusion solutions or—during kidney substitute therapy—so-called dialysis solutions are often used in medical treatment systems. These solutions are preferably supplied in sterile packaging in containers or flexible pouches or they are manufactured on site in storage containers. The storage containers are connected to the treatment system via a connector so that the solution is available during treatment. It is of particular interest here that the connector is initially closed until the solution reaches the point of application in order then to be switched to an opened state. To prevent a premature accidental leaking of the solution, a manual opening by the operator should be avoided during normal handling.

For this reason, connectors or adapters have been developed, which are only opened manually after the connection or assembly of a hose system. The connector in accordance with the invention also belongs to this type, but has the advantage that the flow is opened simultaneously with the connection to the machine, whereas a seal against the environment is ensured beforehand. This effect is achieved by an inner piston which can be axially displaced exactly one time in a cylindrical housing by a corresponding counter-piece at the machine. On connection to the machine, an inner, displaceable piston is pushed into the front part of the connector and thus the flow aperture released for the passing through of fluid.

The connector is preferably made of plastic, particularly formed from two different plastic materials. While the outer connector part is made of polypropylene, in particular for connection to other polyolefin materials, the displaceable inner part should be made of silicone rubber. The whole connector is thus a disposable part, also in connection with the hose system, which can be made at low cost in an injection moulding process and in a simple design due to the simple assembly of the two components. The error-proneness is naturally also extremely reduced by the low number of components.

In addition to the simple handling for the user, which requires no additional hand movement such as breaking off a pin, screwing or turning, it is also reliably prevented that particles enter the continuing hose system.

Since no object lies in the continuing line in an undefined manner, the same flow is always ensured, as the inner piston is always pushed in to the same, identical position and releases the defined flow aperture thanks to its stop. The flow aperture can be formed by one or more lateral openings which are located in a first, closed state in a section of the connector which has such a narrow lumen that the flow apertures contact sealingly or lie upstream of this tapered position at which the displacement member sealingly contacts the inside of the connector. In a second, open state, the displacement member is pushed into a region of the connector which has a larger inner diameter. In this way, the flow apertures move into a region downstream of the tapered position and are released for the flow.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Further details and advantages of the invention can be seen from the following description of preferred embodiments of the invention.

Figure 1:
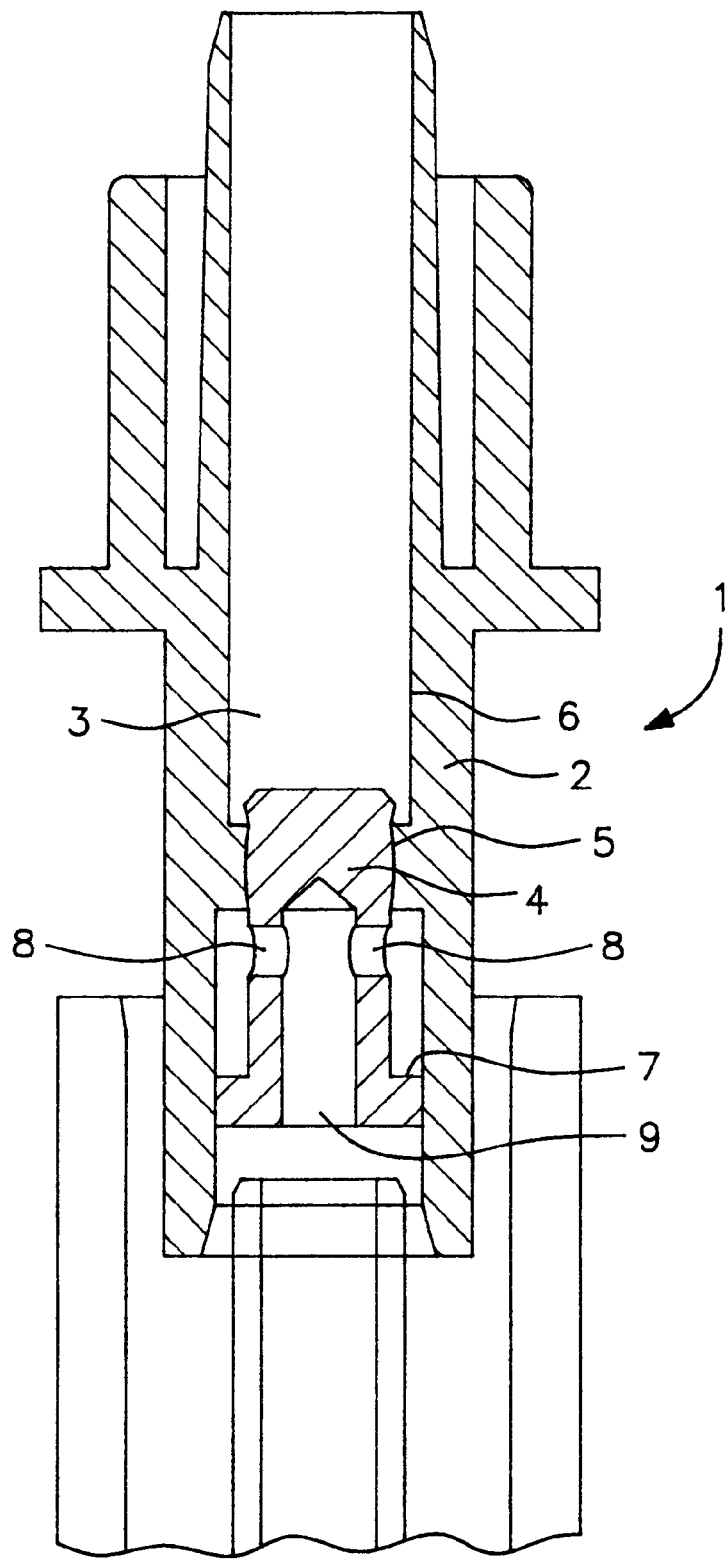
FIG. 1 illustrates a connector in accordance with the present invention, shown with a closed outlet.

FIG. 1 shows a connector 1 designed in accordance with an embodiment of the invention having a closed outlet. The cylindrical body 2 surrounds a hollow lumen 3 in which a displacement member 4 is movably supported, with the lumen 3 having at least one lumen region 5 tapered in diameter and one lumen region 6 at a distance thereto. The tapered lumen region 5 preferably simultaneously serves as a stop area for the stop 7. Furthermore, the displacement member 4 has at least one flow aperture 8. The flow aperture 8 is above the tapered position 5 in the embodiment shown. However, an embodiment is also feasible which shows the aperture 8 at the height of the tapered position 5 so that the inside 5 of the connector 1 simultaneously provides the sealing of the flow aperture 8. Additional seals, in particular O-ring seals, are feasible at the tapered position.

Figure 2:
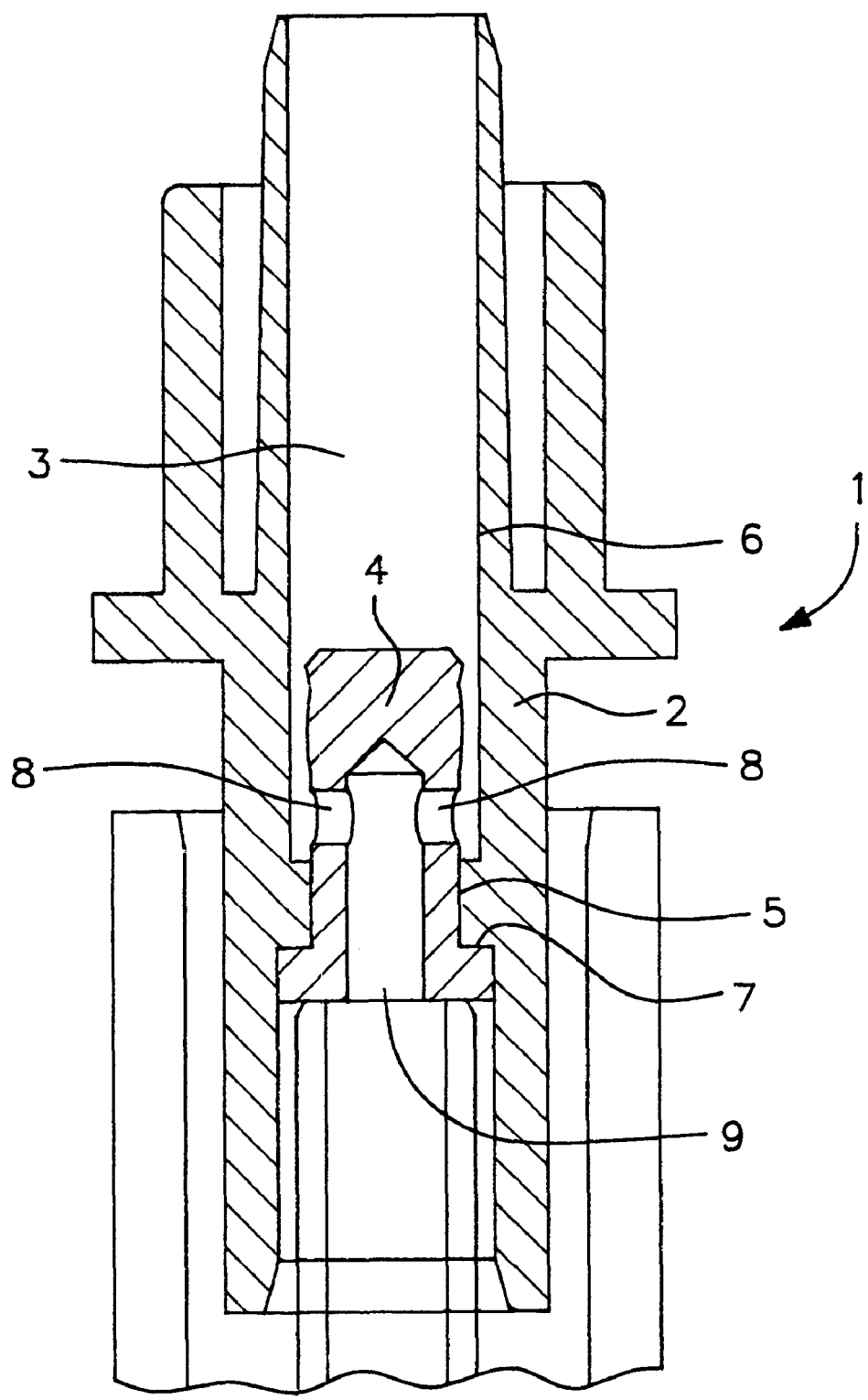
FIG. 2 illustrates the connector of FIG. 1, but positioned with the outlet opened for flow.

FIG. 2 shows the connector 1 in accordance with the invention in the state opened for flow. The inner displacement member 4 is displaced into a second position. The same reference numerals are used. In this figure, the stop 7 contacts the stop surface and thus prevents the displacement member 4 from slipping further. The flow aperture 8 is located downstream of the tapered position 5 in the lumen part 3 so that a flow is effected through the gap which is formed between the inner wall 6 of the connector 1 and the displacement member 4. To allow the flow, the solution enters the inner hollow space 9 of the displacement member in order to exit to the outside through the flow aperture 8. The invention is, however, not restricted to this embodiment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A connector having hose connections at a proximal end and a distal end, said connector comprising:

a generally cylindrical body surrounding a hollow lumen that allows flow therethrough to an outlet aperture, said lumen including a tapered region;

an inner displacement member supported within said lumen and having a flow aperture therein, an outer end portion of said displacement member opposite said outlet aperture for being pushed to move said displacement member axially from a first position in which fluid is prevented from flowing through said aperture by said tapered region, to a second position in which said flow aperture is irreversibly opened for fluid flow therethrough, said connector being free of any means for moving said displacement member back from said second position to said first position.

2. The connector in accordance with claim 1, wherein said displacement member includes a stop that defines said second position, said stop contacting said tapered region to prevent further axial movement upon displacement of said displacement member from said first position to said second position.

3. The connector in accordance with claim 1, wherein said connector is made of plastic and is a disposable article.

4. The connector in accordance with claim 3, wherein said displacement member is made of silicone rubber.

5. The connector in accordance with claim 1, wherein said displacement member is displaceable from said first position to said second position exactly one time.

6. A connector having hose connections at a proximal end and a distal end thereof for connection to a hose system, said connector comprising:

a housing surrounding a hollow lumen that allows flow therethrough, said lumen including a tapered region;

an inner displacement member supported within said lumen and having a stop and a flow aperture therein, said displacement member starting in a first position in which said tapered region prevents fluid from flowing through said aperture and, simultaneously with said connector being connected to said hose system, said displacement member being axially and irreversibly moved through contact with a corresponding component of said hose system to a second position in which said flow aperture is unobstructed by said tapered region and thereby opened for fluid flow through said aperture, said stop contacting said tapered region to prevent further axial movement upon displacement of said displacement member from said first position to said second position, said connector being free of any means for returning said displacement member to said first position such that said displacement member is displaceable from said first position to said second position only one time.

7. The connector in accordance with claim 6, wherein said connector is made of plastic and, being designed for a single use, is a disposable article.

8. The connector in accordance with claim 7, wherein said displacement member is made of silicone rubber.

* * * * *